(12) United States Patent
O'Neil

(10) Patent No.: US 9,371,363 B2
(45) Date of Patent: Jun. 21, 2016

(54) PEPTIDES AND THEIR USE

(75) Inventor: Deborah O'Neil, Aberdeen (GB)

(73) Assignee: Novabiotics Limited, Aberdeen (GB)

( * ) Notice: Subject to any disclaimer, the term of this patent is extended or adjusted under 35 U.S.C. 154(b) by 992 days.

(21) Appl. No.: 12/525,519

(22) PCT Filed: Jan. 28, 2008

(86) PCT No.: PCT/GB2008/000281
§ 371 (c)(1), (2), (4) Date: Oct. 15, 2009

(87) PCT Pub. No.: WO2008/093058
PCT Pub. Date: Aug. 7, 2008

(65) Prior Publication Data
US 2010/0047186 A1    Feb. 25, 2010

Related U.S. Application Data

(60) Provisional application No. 60/899,149, filed on Feb. 2, 2007.

(30) Foreign Application Priority Data

Feb. 2, 2007 (GB) .................................. 0702021.7

(51) Int. Cl.
  *A61K 9/12* (2006.01)
  *C07K 7/08* (2006.01)
  *C07K 7/06* (2006.01)
  *C07K 14/00* (2006.01)

(52) U.S. Cl.
  CPC ... *C07K 7/08* (2013.01); *C07K 7/06* (2013.01); *C07K 14/00* (2013.01)

(58) Field of Classification Search
  CPC ............. C07K 14/00; C07K 7/06; C07K 7/08
  See application file for complete search history.

(56) References Cited

U.S. PATENT DOCUMENTS

| | | |
|---|---|---|
| 7,847,059 B2 * | 12/2010 | O'Neil .......................... 530/300 |
| 2005/0107289 A1 * | 5/2005 | Ghadiri et al. .................... 514/9 |
| 2005/0192210 A1 * | 9/2005 | Rothbard et al. ................. 514/2 |
| 2005/0277589 A1 | 12/2005 | Arranz |
| 2006/0166867 A1 * | 7/2006 | Lapidot et al. .................... 514/8 |

FOREIGN PATENT DOCUMENTS

| | | | | |
|---|---|---|---|---|
| EP | 1 502 949 A1 * | 2/2005 | ............. | C12N 15/09 |
| WO | 2005/068645 A2 | 7/2005 | | |
| WO | WO 2005/068645 * | 7/2005 | ............. | C12P 21/00 |
| WO | 2006/018652 A2 | 2/2006 | | |
| WO | 2008/093059 A1 | 8/2008 | | |
| WO | 2008/093060 A2 | 8/2008 | | |

OTHER PUBLICATIONS

Strom, Morten B. et al., "Antimicrobial Activity of Short Arginine- and Tryptophan-rich Peptides," Journal of Peptide Society, John Wiley & Sons, Ltd., vol. 8, pp. 431-437 (2002).

* cited by examiner

*Primary Examiner* — Suzanne Ziska
(74) *Attorney, Agent, or Firm* — Morgan, Lewis & Bockius LLP

(57) ABSTRACT

The invention relates to peptides, and peptide variants thereof, in which substantially all of the amino acids in the amino sequence of said peptide are the same, for use as antibacterial agents.

11 Claims, No Drawings

SEQUENCE LISTING

<160> NUMBER OF SEQ ID NOS: 35

<210> SEQ ID NO 1
<211> LENGTH: 5
<212> TYPE: PRT
<213> ORGANISM: Artificial
<220> FEATURE:
<223> OTHER INFORMATION: synthetic peptide

<400> SEQUENCE: 1

Arg Val Arg Val Arg
1               5

<210> SEQ ID NO 2
<211> LENGTH: 5
<212> TYPE: PRT
<213> ORGANISM: Artificial
<220> FEATURE:
<223> OTHER INFORMATION: synthetic peptide

<400> SEQUENCE: 2

Arg Arg Val Val Arg
1               5

<210> SEQ ID NO 3
<211> LENGTH: 5
<212> TYPE: PRT
<213> ORGANISM: Artificial
<220> FEATURE:
<223> OTHER INFORMATION: synthetic peptide

<400> SEQUENCE: 3

Arg Arg Val Arg Arg
1               5

<210> SEQ ID NO 4
<211> LENGTH: 6
<212> TYPE: PRT
<213> ORGANISM: Artificial
<220> FEATURE:
<223> OTHER INFORMATION: synthetic peptide

<400> SEQUENCE: 4

Arg Arg Val Arg Val Arg
1               5

<210> SEQ ID NO 5
<211> LENGTH: 6
<212> TYPE: PRT
<213> ORGANISM: Artificial
<220> FEATURE:
<223> OTHER INFORMATION: synthetic peptide

<400> SEQUENCE: 5

Arg Arg Val Val Arg Arg
1               5

<210> SEQ ID NO 6
<211> LENGTH: 7
<212> TYPE: PRT
<213> ORGANISM: Artificial
<220> FEATURE:
<223> OTHER INFORMATION: synthetic peptide

<400> SEQUENCE: 6

Arg Arg Arg Val Arg Arg Arg
1               5

<210> SEQ ID NO 7
<211> LENGTH: 7
<212> TYPE: PRT
<213> ORGANISM: Artificial
<220> FEATURE:
<223> OTHER INFORMATION: synthetic peptide

<400> SEQUENCE: 7

Arg Arg Val Arg Val Arg Arg
1               5

<210> SEQ ID NO 8
<211> LENGTH: 8
<212> TYPE: PRT
<213> ORGANISM: Artificial
<220> FEATURE:
<223> OTHER INFORMATION: synthetic peptide

<400> SEQUENCE: 8

Arg Arg Arg Val Val Arg Arg Arg
1               5

<210> SEQ ID NO 9
<211> LENGTH: 8
<212> TYPE: PRT
<213> ORGANISM: Artificial
<220> FEATURE:
<223> OTHER INFORMATION: synthetic peptide

<400> SEQUENCE: 9

Arg Arg Val Arg Arg Val Arg Arg
1               5

<210> SEQ ID NO 10
<211> LENGTH: 10
<212> TYPE: PRT
<213> ORGANISM: Artificial
<220> FEATURE:
<223> OTHER INFORMATION: synthetic peptide

<400> SEQUENCE: 10

Arg Arg Arg Arg Val Val Arg Arg Arg Arg
1               5                   10

<210> SEQ ID NO 11
<211> LENGTH: 10
<212> TYPE: PRT
<213> ORGANISM: Artificial
<220> FEATURE:
<223> OTHER INFORMATION: synthetic peptide

<400> SEQUENCE: 11

Arg Arg Val Val Arg Arg Val Val Arg Arg
1               5                   10

<210> SEQ ID NO 12
<211> LENGTH: 9
<212> TYPE: PRT
<213> ORGANISM: Artificial
<220> FEATURE:
<223> OTHER INFORMATION: synthetic peptide

<400> SEQUENCE: 12

Arg Arg Arg Arg Arg Arg Arg Arg Arg
1               5

<210> SEQ ID NO 13
<211> LENGTH: 11
<212> TYPE: PRT
<213> ORGANISM: Artificial
<220> FEATURE:
<223> OTHER INFORMATION: synthetic peptide

<400> SEQUENCE: 13

Arg Arg Arg Arg Arg Arg Arg Arg Arg Arg Arg
1               5                   10

<210> SEQ ID NO 14
<211> LENGTH: 13
<212> TYPE: PRT
<213> ORGANISM: Artificial
<220> FEATURE:
<223> OTHER INFORMATION: synthetic peptide

<400> SEQUENCE: 14

Arg Arg Arg Arg Arg Arg Arg Arg Arg Arg Arg Arg Arg
1               5                   10

<210> SEQ ID NO 15
<211> LENGTH: 15
<212> TYPE: PRT
<213> ORGANISM: Artificial
<220> FEATURE:
<223> OTHER INFORMATION: synthetic peptide

<400> SEQUENCE: 15

Arg Arg Arg Arg Arg Arg Arg Arg Arg Arg Arg Arg Arg Arg Arg
1               5                   10                  15

<210> SEQ ID NO 16
<211> LENGTH: 5
<212> TYPE: PRT
<213> ORGANISM: Artificial
<220> FEATURE:
<223> OTHER INFORMATION: synthetic peptide

<400> SEQUENCE: 16

Arg Trp Arg Trp Arg
1               5

<210> SEQ ID NO 17
<211> LENGTH: 5
<212> TYPE: PRT
<213> ORGANISM: Artificial
<220> FEATURE:
<223> OTHER INFORMATION: synthetic peptide

<400> SEQUENCE: 17

Arg Arg Trp Trp Arg
1               5

<210> SEQ ID NO 18
<211> LENGTH: 5
<212> TYPE: PRT
<213> ORGANISM: Artificial
<220> FEATURE:
<223> OTHER INFORMATION: synthetic peptide

<400> SEQUENCE: 18

Arg Arg Trp Arg Arg
1               5

```
<210> SEQ ID NO 19
<211> LENGTH: 6
<212> TYPE: PRT
<213> ORGANISM: Artificial
<220> FEATURE:
<223> OTHER INFORMATION: synthetic peptide

<400> SEQUENCE: 19

Arg Arg Trp Arg Trp Arg
1               5

<210> SEQ ID NO 20
<211> LENGTH: 6
<212> TYPE: PRT
<213> ORGANISM: Artificial
<220> FEATURE:
<223> OTHER INFORMATION: synthetic peptide

<400> SEQUENCE: 20

Arg Arg Trp Trp Arg Arg
1               5

<210> SEQ ID NO 21
<211> LENGTH: 7
<212> TYPE: PRT
<213> ORGANISM: Artificial
<220> FEATURE:
<223> OTHER INFORMATION: synthetic peptide

<400> SEQUENCE: 21

Arg Arg Arg Trp Arg Arg Arg
1               5

<210> SEQ ID NO 22
<211> LENGTH: 7
<212> TYPE: PRT
<213> ORGANISM: Artificial
<220> FEATURE:
<223> OTHER INFORMATION: synthetic peptide

<400> SEQUENCE: 22

Arg Arg Trp Arg Trp Arg Arg
1               5

<210> SEQ ID NO 23
<211> LENGTH: 7
<212> TYPE: PRT
<213> ORGANISM: Artificial
<220> FEATURE:
<223> OTHER INFORMATION: synthetic peptide

<400> SEQUENCE: 23

Arg Arg Arg Arg Arg Arg Arg
1               5

<210> SEQ ID NO 24
<211> LENGTH: 8
<212> TYPE: PRT
<213> ORGANISM: Artificial
<220> FEATURE:
<223> OTHER INFORMATION: synthetic peptide

<400> SEQUENCE: 24

Arg Arg Trp Arg Arg Trp Arg Arg
1               5

<210> SEQ ID NO 25
```

```
<211> LENGTH: 12
<212> TYPE: PRT
<213> ORGANISM: Artificial
<220> FEATURE:
<223> OTHER INFORMATION: synthetic peptide

<400> SEQUENCE: 25

Gly Lys Lys Glu Lys Pro Glu Lys Lys Val Lys Lys
1               5                   10

<210> SEQ ID NO 26
<211> LENGTH: 16
<212> TYPE: PRT
<213> ORGANISM: Artificial
<220> FEATURE:
<223> OTHER INFORMATION: synthetic peptide

<400> SEQUENCE: 26

Lys Leu Thr Lys Pro Lys Pro Gln Ala Glu Ser Lys Lys Lys Lys Lys
1               5                   10                  15

<210> SEQ ID NO 27
<211> LENGTH: 15
<212> TYPE: PRT
<213> ORGANISM: Artificial
<220> FEATURE:
<223> OTHER INFORMATION: synthetic peptide

<400> SEQUENCE: 27

Lys Lys Lys Lys Lys Glu Gly Lys Lys Gln Glu Lys Met Leu Asp
1               5                   10                  15

<210> SEQ ID NO 28
<211> LENGTH: 8
<212> TYPE: PRT
<213> ORGANISM: Artificial
<220> FEATURE:
<223> OTHER INFORMATION: synthetic peptide

<400> SEQUENCE: 28

Lys Lys Lys Asp Lys Val Lys Lys
1               5

<210> SEQ ID NO 29
<211> LENGTH: 11
<212> TYPE: PRT
<213> ORGANISM: Artificial
<220> FEATURE:
<223> OTHER INFORMATION: synthetic peptide

<400> SEQUENCE: 29

Lys Val Arg Gln Gly Thr Leu Lys Lys Ala Arg
1               5                   10

<210> SEQ ID NO 30
<211> LENGTH: 16
<212> TYPE: PRT
<213> ORGANISM: Artificial
<220> FEATURE:
<223> OTHER INFORMATION: synthetic peptide

<400> SEQUENCE: 30

Pro Lys Thr Lys Ala Lys Ala Lys Ala Lys Lys Gly Lys Gly Lys Asp
1               5                   10                  15

<210> SEQ ID NO 31
<211> LENGTH: 13
```

```
<212> TYPE: PRT
<213> ORGANISM: Artificial
<220> FEATURE:
<223> OTHER INFORMATION: synthetic peptide

<400> SEQUENCE: 31

Arg Arg Arg Arg Arg Arg Arg Arg Arg Arg Arg
1               5                   10

<210> SEQ ID NO 32
<211> LENGTH: 5
<212> TYPE: PRT
<213> ORGANISM: Artificial
<220> FEATURE:
<223> OTHER INFORMATION: synthetic peptide

<400> SEQUENCE: 32

Lys Lys Lys Lys Lys
1               5

<210> SEQ ID NO 33
<211> LENGTH: 9
<212> TYPE: PRT
<213> ORGANISM: Artificial
<220> FEATURE:
<223> OTHER INFORMATION: synthetic peptide

<400> SEQUENCE: 33

Lys Lys Lys Lys Lys Lys Lys Lys Lys
1               5

<210> SEQ ID NO 34
<211> LENGTH: 15
<212> TYPE: PRT
<213> ORGANISM: Artificial
<220> FEATURE:
<223> OTHER INFORMATION: synthetic peptide

<400> SEQUENCE: 34

Lys Lys Lys Lys Lys Lys Lys Lys Lys Lys Lys Lys Lys Lys Lys
1               5                   10                  15

<210> SEQ ID NO 35
<211> LENGTH: 7
<212> TYPE: PRT
<213> ORGANISM: Artificial
<220> FEATURE:
<223> OTHER INFORMATION: synthetic peptide

<400> SEQUENCE: 35

Lys Lys Lys Lys Lys Lys Lys
1               5
```

PEPTIDES AND THEIR USE

REFERENCE TO RELATED APPLICATIONS

This application is the US national phase entry of International Patent Application No. PCT/GB2008/000281, filed Jan. 28, 2008, which claims priority to GB Patent Application No. 0702021.7, filed Feb. 2, 2007, and U.S. Provisional Patent Application No. 60/899,149, filed Feb. 2, 2007.

FIELD OF THE INVENTION

This invention relates to peptides and their use in the treatment of bacterial infections.

BACKGROUND TO THE INVENTION

Antimicrobial peptides are key effector molecules of the innate immune system and integral components of the first line of defence against microbial infections of all eukaryotic organisms. A number of prokaryotic organisms also utilise antimicrobial peptides as means to compete against challenge from other microorganisms. Many antimicrobial peptides are characterised by cationic properties that facilitate interactions with the negatively charged phospholipids of the microbial membrane which then lead to microbial lysis and death following subsequent membrane permeabilisation. For example, it has been shown that antimicrobial peptide molecules can aggregate and form voltage dependent channels in the lipid bilayer resulting in the permeabilization of both the inner and outer membrane of the microorganism (Lehrer, R. I., J. Clin. Investigation, 84:553 (1989)). The amphiphilic nature of these molecules may also facilitate the insertion of the hydrophobic residue into the lipid bilayer by electrostatic attraction while the polar residues project into and above the membrane.

Drug resistant microorganisms, especially bacteria, are becoming increasingly problematic as infection rates continue to rise and effective methods of control become more and more limited. Prolific use of antibiotics over the last 50 or so years together with the indiscriminate prescribing of antibiotics and patient non-compliance with treatment regimes, has selected for microorganisms that have developed or acquired ways of overcoming the effects of antibiotics. The transmission and control of drug-resistant organisms is becoming one of the most significant problems within healthcare.

Of particular note are strains of *Staphylococcus* spp. that have developed or obtained varying levels of resistance to antibiotics such as methicillin (meticillin). These strains are commonly known as methicillin resistant *Staphylococcus aureus* (MRSA). In addition, coagulase-negative Staphylococci, such as *Staphylococcus epidermidis*, have also emerged as important nosocomial pathogens. Approximately 80% of *S. epidermidis* isolates from device-associated infections are methicillin resistant (MRSE) as well as being multi-resistant. The treatment options for infections contributed to or caused by methicillin resistant bacteria such as MRSA and MRSE, are now limited and there is an urgent need to discover new therapies which inhibit or kill such organisms.

*Pseudomonas aeruginosa* is an opportunistic pathogen that causes urinary tract infections, respiratory system infections, dermatitis, soft tissue infections, bacteraemia and a variety of systemic infections, particularly in victims of severe burns and in cancer and AIDS patients who are immunosuppressed. Respiratory infections caused by *Pseudomonas aeruginosa* occur almost exclusively in individuals with a compromised lower respiratory tract or a compromised systemic defence mechanism. Primary pneumonia occurs in patients with chronic lung disease and congestive heart failure. Bacteraemic pneumonia commonly occurs in neutropenic cancer patients undergoing chemotherapy. Lower respiratory tract colonisation of cystic fibrosis patients by mucoid strains of *Pseudomonas aeruginosa* is common and difficult to treat. There is a need to develop an effective means of treating *Pseudomonas aeruginosa* infections.

Since microbial pathogens do not readily acquire resistance to cationic peptides, despite evolutionary pressure from millions of years of co-existence, there has been much in the way of commercial interest and effort in developing cationic peptides as potential antimicrobial therapeutics. For example, in our co-pending application, WO 2006/018652, we describe the identification of peptides that can be used to treat microbial infections including certain bacterial infections.

There is still a pressing need for further antimicrobial actives that can be used in the treatment of bacterial infections such as those caused by *Staphylococcal* and *Pseudomonad* strains.

DETAILED DESCRIPTION

The present invention is based in part on the finding that homopolymers of arginine or lysine are highly bactericidal and as such are effective in the treatment of bacterial infections.

According to a first aspect the invention provides a peptide for use as an antibacterial agent wherein substantially all of the amino acids in the amino sequence of said peptide are the same.

In a preferred peptide of the invention the amino acids of said sequence are basic amino acids.

In a preferred peptide the basic amino acids are selected from lysine, arginine and histidine, in particular lysine and arginine. Preferably still the basic amino acid is arginine.

As used herein "substantially" is a relative modifier intended to indicate permissible variation from the characteristic so modified. Specifically, by "substantially all of the amino acids in said amino acid sequence are the same" it is meant that either all, or a high proportion of, the amino acids in the sequence are identical. By "high proportion" it is contemplated that 1 or 2 substitutions may be made in the sequence.

In a preferred aspect the invention provides a peptide, or peptide variant thereof, comprising an amino acid sequence according to the formula (I)

$$(X) \qquad\qquad (I)$$

wherein X is the amino acid arginine or lysine for use as a medicament.

In a peptide of the invention X may be arginine.
In a peptide of the invention X may be lysine.
In a peptide of the invention X may be histidine.
In a preferred aspect of the invention the peptide comprises a sequence of 5 to 15 basic amino acids.

In a preferred aspect the peptide of the invention comprises a sequence of 9 to 15, for example 10 to 15 or 10 to 13, basic amino acids wherein substantially all of the amino acids in said sequence of amino acids are the same. Preferably still the peptide of the invention comprises a sequence of 9 to 13, for example 11 to 13, basic amino acids wherein substantially all of the amino acids in said sequence are the same.

In a further preferred aspect the invention provides a peptide, or peptide variant thereof, comprising an amino acid sequence according to the formula (II)

$$(X)_n \quad (II)$$

wherein X is the amino acid arginine or lysine and n is an integer between 5 and 15, for use as a medicament.

In a preferred peptide of the invention X is arginine.

In a peptide of the invention n may be between 9 and 15 e.g. 9, 10, 11, 12, 13, 14 or 15. In a preferred peptide of the invention n is an integer between 9 and 14, for example between 11 and 14. Preferably n is 13 or 14.

In a peptide of formula (I), X may be a D- or L-amino acid.

In a preferred aspect the invention provides a linear peptide consisting of amino acids according to formula (I).

The invention also includes known isomers (structural, stereo-, conformational & configurational) and structural analogues of the above amino acids, including peptidomimetics, and those modified either naturally (e.g. post-translational modification) or chemically, including, but not exclusively, phosphorylation, glycosylation, sulfonylation and/or hydroxylation.

In addition, the amino acid sequence of the peptide can be modified so as to result in a peptide variant that includes the substitution of at least one amino acid residue in the peptide for another amino acid residue, for example a basic or non-basic residue, including substitutions that utilise the D rather than L form, wherein the variant retains some (typically at least 10%) or all of the biological activity of the corresponding non-variant peptide. Thus the invention provides a peptide variant in which one or more lysine or arginine residues of formula (I) is substituted by one or more different (e.g. histidine) residues.

The term "peptide" as used herein means, in general terms, a plurality of amino acid residues joined together by peptide bonds. It is used interchangeably and means the same as polypeptide, oligopeptide and protein.

The peptides of the invention generally are synthetic peptides. The peptides may be isolated, purified peptides or variants thereof, which can be synthesised in vitro, for example, by a solid phase peptide synthetic method, by enzyme catalysed peptide synthesis, or with the aid of recombinant DNA technology.

The peptides of the invention can exist in different forms, such as free acids, free bases, esters and other prodrugs, salts and tautomers, for example, and the invention includes all variant forms of the peptides. Thus, the invention encompasses the salt or pro-drug of a peptide.

The peptide of the invention may be administered in the form of a pharmaceutically acceptable salt. The invention thus includes pharmaceutically-acceptable salts of the peptide of the invention wherein the parent compound is modified by making acid or base salts thereof for example the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, oxalate, palmoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glutamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

Salts of carboxyl groups of a peptide or peptide variant of the invention may be prepared in the usual manner by contacting the peptide with one or more equivalents of a desired base such as, for example, a metallic hydroxide base, e.g sodium hydroxide; a metal carbonate or bicarbonate such as, for example, sodium carbonate or bicarbonate; or an amine base such as, for example, triethylamine, triethanolamine and the like.

Administration and Pharmaceutical Formulations

A further aspect of the invention provides a pharmaceutical composition comprising a pharmaceutically effective amount of a peptide of the invention.

The composition also includes a pharmaceutically acceptable carrier, excipient or diluent. The phrase "pharmaceutically acceptable" is employed herein to refer to those compounds, materials, compositions, and/or dosage forms which are, within the scope of sound medical judgment, suitable for use in contact with the tissues of human beings or, as the case may be, an animal without excessive toxicity, irritation, allergic response, or other problem or complication, commensurate with a reasonable benefit/risk ratio.

To achieve the desired effect(s), the peptide, a variant thereof or a combination thereof, may be administered as single or divided dosages, for example, of at least about 0.01 mg/kg to about 500 to 750 mg/kg, of at least about 0.01 mg/kg to about 300 to 500 mg/kg, at least about 0.1 mg/kg to about 100 to 300 mg/kg or at least about 1 mg/kg to about 50 to 100 mg/kg of body weight or at least about 1 mg/kg to about 20 mg/kg of body weight, although other dosages may provide beneficial results.

To prepare the composition, peptides are synthesized or otherwise obtained, purified as necessary or desired, and then lyophilized and stabilized. The peptide can then be adjusted to the appropriate concentration and optionally combined with other agents.

Thus, one or more suitable unit dosage forms comprising the therapeutic peptides of the invention can be administered by a variety of routes including oral, topical, parenteral (including subcutaneous, intravenous, intramuscular and intraperitoneal), vaginal, rectal, dermal, transdermal, intrathoracic, intrapulmonary and intranasal (respiratory) routes. The therapeutic peptides may also be formulated in a lipid formulation or for sustained release (for example, using microencapsulation, see WO 94/07529, and U.S. Pat. No. 4,962,091). The formulations may, where appropriate, be conveniently presented in discrete unit dosage forms and may be prepared by any of the methods well-known to the pharmaceutical arts. Such methods may include the step of mixing the therapeutic agent with liquid carriers, solid matrices, semi-solid carriers, finely divided solid carriers or combinations thereof, and then, if necessary, introducing or shaping the product into the desired delivery system.

When the therapeutic peptides of the invention are prepared for oral administration, they are generally combined with a pharmaceutically acceptable carrier, diluent or excipient to form a pharmaceutical formulation, or unit dosage form. For oral administration, the peptides may be present as a powder, a granular formation, a solution, a suspension, an emulsion.

Pharmaceutical formulations containing the therapeutic peptides of the invention can be formulated with common excipients, diluents, or carriers, and formed into tablets, capsules, solutions, suspensions, powders, aerosols and the like.

The therapeutic peptides of the invention can also be formulated as elixirs or solutions for convenient oral administration or as solutions appropriate for parenteral administration, for instance by intramuscular, subcutaneous, intraperitoneal or intravenous routes. The pharmaceutical formulations of the therapeutic peptides of the invention can also take the form of an aqueous or anhydrous solution or dispersion, or alternatively the form of an emulsion or suspension or salve.

The therapeutic peptides may be formulated for parenteral administration (e.g. by injection, for example, bolus injection or continuous infusion) and may be presented in unit dose form in ampules, pre-filled syringes, small volume infusion containers or in multi-dose containers.

These formulations can contain pharmaceutically acceptable carriers, vehicles and adjuvants that are well-known in the art. It is possible, for example, to prepare solutions using one or more organic solvent(s) that is/are acceptable from the physiological standpoint, chosen, in addition to water, from solvents such as acetone, acetic acid, ethanol, isopropyl alcohol, dimethyl sulphoxide, glycol ethers such as the products sold under the name "Dowanol", polyglycols and polyethylene glycols, $C_1$-$C_4$ alkyl esters of short-chain acids, ethyl or isopropyl lactate, fatty acid triglycerides such as the products marketed under the name "Miglyol", isopropyl mytrisate, animal, mineral and vegetable oils and polysiloxanes.

A preferred route of administration is topical. For topical administration, the peptides may be formulated as is known in the art for direct application to a target area, for example nails and skin. Forms chiefly conditioned for topical application take the form, for example, of laquers, creams, milks, gels, powders, dispersion or microemulsions, lotions thickened to a greater or lesser extent, impregnated pads, ointments or sticks, aerosol formulations (e.g. sprays or foams), soaps, detergents, lotions or cakes of soap. Other conventional forms for this purpose include wound dressings, coated bandages or other polymer coverings, ointments, creams, lotions, pastes, jellies, sprays, and aerosols. Thus, the therapeutic peptides of the invention can be delivered via patches or bandages for dermal administration.

It may be possible to administer a peptide of the invention transdermally via, for example, some form of transdermal delivery device. Such devices are advantageous, particularly for the administration of antibiotic compounds, as they may allow a prolonged period of treatment relative to for example, an oral or intravenous medicament. Examples of transdermal delivery devices may include, for example, a patch, dressing, bandage or plaster adapted to release the peptide through the skin of a patient. A person of skill in the art would be familiar with the materials and techniques which may be used to transdermally deliver a compound or substance and exemplary transdermal delivery devices are provided by GB2185187, U.S. Pat. No. 3,249,109, U.S. Pat. No. 3,598, 122, U.S. Pat. No. 4,144,317, U.S. Pat. No. 4,262,003 and U.S. Pat. No. 4,307,717. By way of example, a peptide of the invention may be combined with some form of matrix or substrate, such as a non-aqueous polymeric carrier, to render it suitable for use in a transdermal delivery system. The peptide/matrix or substrate mixture may be further strengthened by the use of a woven or knit, non-woven, relatively open mesh fabric, to produce a patch, bandage, plaster or the like which may be temporarily attached to a particular region of a patient's body. In this way, while in contact with a patient's skin, the transdermal delivery device releases the compound or substance directly to the site of infection or through the skin as required.

The peptides of the invention may also be used as sterilising or cleaning aids for use, for example, on surfaces to reduce and/or eliminate contamination by bacteria. For example, peptides of the present invention may be added to or diluted in an appropriate excipient or solution prior to use as a sterilising or cleaning agent. Exemplary excipients are described above. Such sterilising or cleaning solutions may be used to decontaminate, for example, furniture, floors, equipment including for example specialised hospital equipment and/or surgical equipment. In a further embodiment, the peptides of the invention may be used to eliminate and/or reduce bacterial contamination on parts of the body, particularly for example, the hands. The peptide may be diluted as an aqueous or non-aqueous solution (dissolved in aqueous, non aqueous or organic solvent) and which may be applied to a body part, for example the hands.

The peptides of the invention can also be administered to the respiratory tract. Thus, the present invention also provides aerosol pharmaceutical formulations and dosage forms for use in the methods of the invention. In general, such dosage forms comprise an amount of at least one of the agents of the invention effective to treat or prevent the clinical symptoms of a specific infection, indication or disease. Any statistically significant attenuation of one or more symptoms of an infection, indication or disease that has been treated pursuant to the method of the present invention is considered to be a treatment of such infection, indication or disease within the scope of the invention.

The peptides of the invention may be provided as a combination therapy together with one or more known antimicrobial agents. Typically the peptides of the invention are provided as a monotherapy for the treatment of an infection.

Use

The peptides of the invention may be useful in the treatment or prevention of a variety of bacterial infections.

Thus a further aspect of the invention provides the use of a peptide according to the invention, or a pharmaceutically acceptable salt thereof, in the manufacture of a medicament for the treatment or alleviation of an infection contributed to or caused by a *bacterium*. The *bacterium* may be a Gram negative or a Gram positive *bacterium*.

In a use according to the invention the bacterial infection may be caused by a *bacterium* selected from the group consisting of, but not limited to, *Abiotropha* spp, *Achromobacter* spp, *Acidaminacoccus* spp, *Acinetobacter* spp, *Actinobacillus* spp, *Actinomadura* spp, *Actinomyces* spp, *Aerococcus* spp, *Aeromonas* spp, *Alcaligenes*, spp, *Anaerovibrio* spp, *Anaplasma* spp, *Arcanobacterium* spp, *Arthrobacter* spp, *Bacillus* spp, *Bacteroides* spp, *Bartonella* spp, *Bordatella* spp, *Bordetella* spp, *Borrelia* spp, *Brachyspira* spp, *Brucella* spp, *Burkholderia* spp, *Calymmatobacterium* spp, *Campylobacter* spp, *Capnocytophaga* spp, *Cardiobacterium* spp, *Catonella* spp, *Chlamydia* spp, *Chryseobacterium* spp, *Citrobacter* spp, *Clostridium* spp, *Corynebacterium* spp, *Coxiella* spp, *Dermabacter* spp, *Desulfovibrio* spp, *Dialister* spp, *Dolosicoccus* spp, *Dolosigranulum* spp, *Edwardsiella* spp, *Eggerthella* spp, *Ehrlichia* spp, *Eikinella* spp, *Empedobacter* spp, *Enterobacter* spp, *Enterococcus* spp, *Erysipelothrix* spp, *Escherichia* spp, *Eubacterium* spp, *Facklamia* spp, *Filifactor* spp, *Flavimonas* spp, *Flavobacterium* spp, *Fluoribacter* spp, *Francisella* spp, *Fusobacterium* spp, *Gardnerella* spp,

*Gemella* spp, *Globicatella* spp, *Granulicatella* spp, *Haemophilus* spp, *Hafnia* spp, *Helicobacter* spp, *Helococcus* spp, *Ignavigranum* spp, *Inquilinus* spp, *Kingella* spp, *Klebsiella* spp, *Kluyvera* spp, *Kytococcus* spp, *Lactobacillus* spp, *Lactococcus* spp, *Legionella* spp, *Leptospira* spp, *Leptotrichia* spp, *Leuconostoc* spp, *Listeria* spp, *Megasphaera* spp, *Micrococcus* spp, *Micropolyspora* spp, *Mobiluncus* spp, *Moraxella* spp, *Morganella* spp, *Mycobacterium* spp, *Mycoplasma* spp, *Myroides* spp, *Neisseria* spp, *Nocardia* spp, *Orientia* spp, *Pandoraea* spp, *Pasteurella* spp, *Pediococcus* spp, *Peptostreptococcus* spp, *Photorhabdus* spp, *Plesiomonas* spp, *Porphyromonas* spp, *Prevotella* spp, *Propionibacterium* spp, *Proteus* spp, *Providencia* spp, *Pseudomonas* spp, *Ralstonia* spp, *Rhizobium* spp, *Rhodococcus* spp, *Rickettsia* spp, *Rochalimaea* spp, *Roseomonas* spp, *Rothia* spp, *Salmonella* spp, *Selenomonas* spp, *Serpulina* spp, *Serratia* spp, *Shigella* spp, *Sneathia* spp, *Staphylococcus* spp, *Stenotrophomonas* spp, *Streptobacillus* spp, *Steptococcus* spp, *Streptomyces* spp, *Streptophomonas* spp, *Thermoactinomyces* spp, *Thermomonospora* spp, *Treponema* spp, *Tropheryma* spp, *Ureaplasma* spp, *Vagococcus* spp, *Veillonella* spp, *Vibrio* spp, *Weisella* spp, *Williamsia* spp, *Yersinia* spp In a use according to the invention the bacterial infection may be caused by, or associated with, *Staphylococcus* spp for example *Staphylococcus aureus* or *Staphylococcus epidermidis*. The *Staphylococcus aureus* infection may be a methicillin resistant or methicillin sensitive strain of *Staphylococcus aureus*.

In a use according to the invention the bacterial infection may be caused by, or associated with, *Pseudomonas* spp for example, *Pseudomonas aeruginosa*.

In a use according to the invention the bacterial infection may be caused by, or associated with, *Propionibacterium* spp for example *Propionibacterium acnes*.

In a use according to the invention the bacterial infection may be caused by, or associated with, a nosocomial bacterial pathogen for example *Staphylococcus* spp (e.g. *Staphylococcus aureus* or *Staphylococcus epidermidis*) or *Pseudomonas* spp (e.g. *Pseudomonas aeruginosa*).

The invention further provides the use of a peptide of the invention, or a pharmaceutically acceptable salt thereof, in the manufacture of a medicament for the treatment or alleviation of a disease or condition contributed to or caused by a bacterial infection.

The disease or condition may be caused by, or associated with, a Gram positive bacterial infection, for example boils, furuncles, cellulitis, impetigo, nocosomial infections, bacteremia, pneumonia, osteomyelitis, endocarditis, meningitis, abcesses, cystic fibrosis, gastrointestinal infections, genitourinary infections, septicemia, pharyngitis, necrotizing fasciitis, acute glomerulonephritis, otilis media, wound infections (including burns), anthrax, encephalitis, diphtheria, gas gangrene, botulism and tetanus.

The disease or condition may be caused by, or associated with, a gram negative bacterial infection include gonorrhea, meningitis, pneumonia, otitis media, osteomyelitis, cystic fibrosis, genitourinary infections, peritonitis, conjunctivitis, septicaemia, venereal disease, bacteremia, nosocomial infections, dysentery, gastrointestinal infections, typhoid fever, pneumonic plague, wound infections, cholera, kidney infections, meliodiosis, conjunctivitis, pertussis, tularemia, brucellosis, Legionnaire's disease, peptic ulcer disease, typhus, pharyngitis.

Other diseases or conditions treatable according to the invention include pyoderma, tuberculosis, leprosy, Buruli ulcers, relapsing fever, Lyme disease, syphilis, respiratory infections, genitourinary infections.

In a use according to the invention the disease or condition to be treated may be an opportunistic bacterial infection for example a bacterial infection caused by a *bacterium* not normally pathogenic, or a bacterial infection caused by a known bacterial pathogen in a body site not normally associated with infection by this bacterial pathogen. For example, an opportunistic infection may be caused by *Staphylococcus* spp for example *Staphylococcus aureus* or *Staphylococcus epidermidis*. In an alternative use the disease or condition to be treated may be an opportunistic bacterial infection for example a bacterial infection caused by, or associated with, *Pseudomonas* spp for example, *Pseudomonas aeruginosa*.

Major clinical diseases in immunocompromised hosts that are contributed to or caused by bacterial infections include, but are not limited to, urinary tract infections, respiratory tract infections, dermatitis, soft tissue infections, bacteremia, bone and joint infections, gastrointestinal infections and a variety of systemic infections in particular in patients with severe burns, cancer, cystic fibrosis or AIDS. The treatment of these diseases is a preferred aspect of the invention.

In one embodiment the invention provides the use of a peptide of formula (I) wherein n is an integer between 11 and 15 (in particular between 11 and 13), or a pharmaceutically acceptable salt thereof, in the manufacture of a medicament for the treatment of a bacterial infection, for example, an opportunistic bacterial infection.

A further aspect of the invention provides a method for the treatment, prevention or delay of progression of a bacterial infection which comprises administering to a patient a therapeutically effective amount of a peptide according to the invention, or a pharmaceutically acceptable salt thereof.

Preferably the patient is a mammal, in particular human.

The bacterial infection treatable by a method of the invention may be an opportunistic infection for example a community acquired infection or a nosocomial infection.

In a preferred method of the invention, the peptide, or pharmaceutically acceptable salt thereof, is intended as a formulation intended for inhalation or parenteral administration.

Thus in one embodiment the invention provides a method for the treatment, prevention or delay of progression of a bacterial infection which comprises administering to a patient a therapeutically effective amount of an aerosol formulation comprising a peptide according to the invention, or a pharmaceutically acceptable salt thereof. The invention further provides an aerosol formulation, including an inhaler comprising said aerosol formulation, comprising a peptide according to the invention, or a pharmaceutically acceptable salt thereof.

In a further embodiment the invention provides a method for the treatment, prevention or delay of progression of a bacterial infection which comprises administering to a patient a therapeutically effective amount of a parenteral formulation comprising a peptide according to the invention, or a pharmaceutically acceptable salt thereof. The invention further provides a parenteral formulation (in particular intravenous) comprising a peptide according to the invention, or a pharmaceutically acceptable salt thereof.

Table 1, the content of which is encompassed by the invention, provides a non-exclusive list of the bacterial infections, and the causative bacteria thereof, that are treatable according to the present invention.

TABLE 1

| Infection | Bacteria |
|---|---|
| *Gram Positive Bacteria:* | |
| Acne Vulgaris | *Propionibacterium acnes* |
| Boils & Furuncles | *Staphylococcus aureus, Staphylococcus epidermidis* |
| Cellulitis | *S aureus, S epidermidis, C perfringens* |
| Impetigo | *S aureus, Streptococcus pyogenes* |
| Nosocomial Infections | *S aureus, S epidermidis, St pyogenes, Enterococci, Clostridium* spp |
| Bacteremia | *S aureus, S epidermidis, St agalactiae, C perfringens, Enterococci* |
| Pneumonia | *S aureus, Micrococcus luteus, St agalactiae, St pneumoniae, Clostridium perfringens* |
| Osteomyelitis | *S aureus, St agalactiae* |
| Endocarditis | *S aureus, M luteus, St pyogenes, St agalactiae, St pneumoniae, Enterococci, Abiotropha* spp., |
| Meningitis | *S aureus, M luteus, St pyogenes, St agalactiae, St pneumoniae, Listeria monocytogenes* |
| Abcesses | *S aureus, M luteus* |
| Cystic Fibrosis | *S aureus* |
| Gastrointestinal Infections | *S aureus, Bacillus cereus, Clostridium* spp |
| Genitourinary Infections | *Staphylococcus saprophyticus, Enterococci* |
| Septicemia | *S aureus, S saprophyticus, St pyogenes, L monocytogenes, C perfringens, Capnocytophaga* spp |
| Pharyngitis | Group A streptococci, *Corynebacterium* spp |
| Necrotising Fasciitis | *S aureus, St pyogenes* |
| Acute Glomerulonephritis | *St pyogenes* |
| Otitis Media | *St pneumoniae* |
| Wound Infections | *S aureus, S epidermidis, Enterococci, Pasteurella multocida, C perfringens* |
| Anthrax | *Bacillus anthracis* |
| Encephalitis | *L monocytogenes* |
| Diphtheria | *Corynebacterium diphtheriae* |
| Gas Gangrene | *Clostridium* spp |
| Botulism | *Clostridium botulinum* |
| Tetanus | *Clostridium tetani* |
| *Gram Negative Bacteria:* | |
| Gonorrhea | *Neisseria gonorrhoeae* |
| Meningitis | *N meningitidis, Haemophilus influenzae, Escherichia coli, Pseudomonas aeruginosa, Stentotrophomonas* spp |
| Pneumonia | *Moraxella catarrhalis, H influenzae, Serratia marcesens, Ps aeruginosa, Acinetobacter* spp |
| Otitis Media | *M catarrhalis, H influenzae* |
| Osteomyelitis | *H influenzae, Ps aeruginosa* |
| Cystic Fibrosis | *Ps aeruginosa, H influenzae, Burkholderia cepacia* complex |
| Genitourinary Infections | *H influenzae, E coli, Klebsiella pneumoniae, Proteus* spp, *Enterobacter aerogenes, Citrobacter* spp, *Ps aeruginosa, Stentotrophomonas* spp |
| Peritonitis | *H influenzae, Stentotrophomonas* spp |
| Conjunctivitis | *H aegyptus, Stentotrophomonas* spp |
| Septicaemia | *H influenzae, K pneumoniae, Enterobacter cloacae, Stentotrophomonas* spp, *Acinetobacter* spp |
| Venereal Disease | *Chlamydia trachomatis, H ducreyi* |
| Bacteraemia | *E coli, Klebsiella* spp, *Enterobacter* spp, *Serratia* spp, *Pr mirabilis, Salmonella* spp, *Citrobacter* spp, *Morganella morganii, Ps aeruginosa, Stentotrophomonas* spp, *Campylobacter* spp |
| Nosocomial Infections | *E coli, Klebsiella pneumoniae, Enterobacter* spp, *Serratia marcesens, Proteus mirabilis, Salmonella* spp, *Citrobacter* spp, *Ps aeruginosa, Stentotrophomonas* spp, *Acinetobacter* spp |
| Dysentry | *Shigella* spp |
| Gastrointestinal Infections | *Shigella* spp, *Escherichia* spp, *Salmonella* spp, *Yersinia* spp, *Aeromonas* spp, *Vibrio* spp, *Campylobacter* spp |
| Typhoid Fever | *Salmonella* spp, *Aeromonas* spp |
| Pneumonic Plague | *Y pestis* |
| Wound Infections | *K pneumoniae, E coli, Enterobacter* spp, *Vibrio* spp, *Ps aeruginosa, Stentotrophomonas* spp, *Acinetobacter* spp |
| Cholera | *Vibrio cholerae, Aeromonas* spp |
| Kidney Infections | *Aeromonas* spp |
| Meliodiosis | *Burkholderia pseudomallei* |
| Conjunctivitis | *Ps aeruginosa, Stentotrophomonas* spp |
| Pertussis | *Bordatella pertussis* |
| Tularemia | *Francisella tularensis* |
| Brucellosis | *Brucella* spp |
| Legionaires' Disease | *Legionella pneumophila* |
| Peptic Ulcer Disease | *Helicobacter pylori* |
| Typhus | *Rickettsia* spp |
| Pharyngitis | *Chlamydia pneumoniae, Neisseria gonorrhoeae* |
| *Other Bacteria:* | |
| Tuberculosis | *Mycobacterium tuberculosis, M bovis* |
| Leprosy | *M leprae* |
| Buruli Ulcers | *M ulcerans* |
| Relapsing Fever | *Borrelia* spp |
| Lyme Disease | *Borrelia* spp |
| Syphilis | *Treponema pallidum* |
| Respiratory Infections | *Mycoplasma pneumoniae* |
| Genitourinary Infections | *Mycoplasma hominis, Ureaplasma* spp |

The diagnosis of specific diseases and conditions treatable according to the invention can be readily determined by the skilled person by the isolation of the causative *bacterium* from blood, tissue, urine etc followed by assaying the bactericidal/bacteristatic effect of the peptide(s).

The extent of protection includes counterfeit or fraudulent products which contain or purport to contain a compound of the invention irrespective of whether they do in fact contain such a compound and irrespective of whether any such compound is contained in a therapeutically effective amount.

Features, integers, characteristics, compounds, chemical moieties or groups described in conjunction with a particular aspect, embodiment or example of the invention are to be understood to be applicable to any other aspect, embodiment or example described herein unless incompatible therewith.

The following Example illustrates the invention.

EXAMPLE

Materials and Methods

All peptides were produced either by solid-phase synthesis under contract by a peptide supplier, NeoMPS SA (Strasbourg, France), or purchased from Sigma-Aldrich Chemical Company Ltd. (Poole, UK).

Sequence of Cationic Peptides

The sequence of the peptides analysed is shown in Table 2. Ac represents an Acetylated modification to the C-terminus of the oligopeptide and NH2 represents an amidation of the N-terminus of the oligopeptide.

Broth Dilution Antibacterial Susceptibility Testing

The sensitivity of relevant bacterial strains to the peptides (was determined using Clinical Laboratory Standard Institute (CLSI; formerly NCCLS) Approved Standards. Bacterial susceptibility was tested using "Methods for Dilution Antimicrobial Susceptibility Tests for Bacteria That Grow Anaerobically; Approved Standard—Seventh Edition M7-A7"

Results

The antibacterial activity of the peptides is shown in Table 2.

TABLE 2

Minimum Inhibitory Concentrations of the peptides against bacteria (all peptides are L isomers, unless indicated otherwise (D). *value in mg/ml).

| | | Antimicrobial activity (mM) | | | | |
|---|---|---|---|---|---|---|
| Identifier | Amino Acid Sequence* | E. coli | S. aureus | Str. pyogenes | P. acnes | Ps. aeruginosa |
| NP301 | RVRVR (SEQ ID NO: 1) | | >2 | | >2 | |
| NP302 | RRVVR (SEQ ID NO: 2) | | >2 | | >2 | |
| NP303 | RRVRR (SEQ ID NO: 3) | | >2 | | >2 | |
| NP304 | RRVRVR (SEQ ID NO: 4) | | >2 | | >2 | |
| NP305 | RRVVRR (SEQ ID NO: 5) | | >2 | | >2 | |
| NP306 | RRRVRRR (SEQ ID NO: 6) | | >2 | | 2 | |
| NP307 | RRVRVRR (SEQ ID NO: 7) | | >2 | | >2 | |
| NP308 | RRRVVRRR (SEQ ID NO: 8) | | >2 | | >2 | |
| NP309 | RRVRRVRR (SEQ ID NO: 9) | | | | 1 | |
| NP310 | RRRRVVRRRR (SEQ ID NO: 10) | | >2 | | 0.5 | |
| NP311 | RRVVRRVVRR (SEQ ID NO: 11) | | >2 | | 2 | |
| NP105 | RRRRRRR (SEQ ID NO: 23) | >2 | >2 | | | |
| NP316 | RRRRRRRRR (SEQ ID NO: 12) | | >2 | | 0.0313 | |
| NP349 | RRRRRRRRR (SEQ ID NO: 12) | | | | | 0.5 |
| NP317 | RRRRRRRRRR (SEQ ID NO: 13) | | 0.25 | | <0.0156 | |
| NP350 | RRRRRRRRRR (SEQ ID NO: 13) | | | | | 0.125 |
| NP318 | RRRRRRRRRRR (SEQ ID NO: 14) | | 0.125 | | <0.0156 | |
| NP351 | RRRRRRRRRRR (SEQ ID NO: 14) | | | | | 0.125 |
| NP319 | RRRRRRRRRRRR (SEQ ID NO: 15) | | 0.125 | | <0.0156 | |
| NP352 | RRRRRRRRRRRR (SEQ ID NO: 15) | | 0.125 | | | 0.0625 |
| NP320 | RWRWR (SEQ ID NO: 16) | | >2 | | 1 | |
| NP321 | RRWWR (SEQ ID NO: 17) | | >2 | | 1 | |
| NP322 | RRWRR (SEQ ID NO: 18) | | >2 | | 2 | |
| NP323 | RRWRWR (SEQ ID NO: 19) | | >2 | | 0.5 | |
| NP324 | RRWWRR (SEQ ID NO: 20) | | 1 | | 0.25 | |
| NP325 | RRRWRRR (SEQ ID NO: 21) | | >2 | | 2 | |
| NP326 | RRWRWRR (SEQ ID NO: 22) | | >2 | | 0.25 | |
| NP328 | RRWRRWRR (SEQ ID NO: 24) | | >2 | | 0.5 | |
| NP331 | GKKEKPEKKVKK (SEQ ID NO: 25) | | >2 | | >2 | |
| NP332 | KLTKPKPQAESKKKKK (SEQ ID NO: 26) | | >2 | | >2 | |
| NP333 | KKKKKEGKKQEKMLD (SEQ ID NO: 27) | | >2 | | >2 | |
| NP334 | KKKDKVKK (SEQ ID NO: 28) | | >2 | | >2 | |
| NP335 | KVRQGTLKKAR (SEQ ID NO: 29) | | >2 | | >2 | |
| NP336 | PKTKAKAKAKKGKGKD (SEQ ID NO: 30) | | >2 | | >2 | |
| NP337 | RRRRRRRRRRRR (SEQ ID NO: 31) | | | | 0.0025 | |
| NP338 | Ac-(RRRRRRRRRRRR)—NH$_2$ (SEQ ID NO: 31) | | | | 0.005 | 0.0625 |
| NP339 | dRdRdRdRdRdRdRdRdRdRdRdR (SEQ ID NO: 31) | | 0.25 | | 0.02 | 0.0625 |
| NP340 | Ac-dRdRdRdRdRdRdRdRdRdRdRdR—NH2 (SEQ ID NO: 31) | | 0.25 | | 0.02 | 0.125 |
| NP341 | dRdRdRdRdRdRdRdRdRdRdRdR—CONH (SEQ ID NO: 31) | | 0.125 | | | 0.0625 |
| NP342 | KKK | | | | >10 | |
| NP343 | KKKKK (SEQ ID NO: 32) | | | | >10 | |
| NP344 | KKKKKKK (SEQ ID NO: 35) | | | | >10 | |
| NP104 | KKKKKKK (SEQ ID NO: 35) | >2 | >2 | 1 | | |
| NP345 | KKKKKKKKK (SEQ ID NO: 33) | | | | 2.5 | |
| NP348 | KKKKKKKKKKKKKK (SEQ ID NO: 34) | | 0.25 | | 0.0625 | |
| NP112 | (K)n, n = 3-14, HBr salt (0.5-2 kDa) | | | | 0.1* | |
| NP106 | (K)n, n = 7-34, HBr salt (1-5 kDa) | | | | 0.125* | |
| NP101 | (K)n, n = 103-205, HCl salt (15-30 kDa) | <0.0313* | | | 0.1* | 0.125* |
| NP121 | (R)n, n = 28-86, HCl salt (5-15 kDa) | 0.0313* | | | 0.01* | 0.0625* |
| NP122 | (R)n, n = 86-402, HCl salt (15-70 kDa) | | | | 0.01* | |
| NP123 | (R)n, n = >402, HCl salt (>70 kDa) | | | | 0.01* | |
| NP131 | (H)n, n = 32-161, HCl salt (5-25 kDa) | >2* | | | >0.1* | |
| NP132 | (H)n, n = >32, HCl salt (>5 kDa) | | | | 0.1* | |

The invention claimed is:

1. A method for the treatment or alleviation of a disease or infection caused by a bacterium in a subject, comprising administering to the subject a peptide, or a pharmaceutically acceptable salt thereof, wherein the peptide comprises 11-14 contiguous arginine residues.

2. The method of claim 1, wherein the bacterium is selected from the group consisting of: *Staphylococcus* spp., *Pseudomonas* spp., and *Propionibacterium* spp.

3. The method of claim 2 wherein the bacterium is *Staphylococcus* spp.

4. The method of claim 2 wherein the bacterium is *Pseudomonas* spp.

5. The method of claim 1 wherein the disease or infection is selected from the group consisting of boils, furuncles, cellulitis, impetigo, nosocomial infections, bacteremia, pneumonia, osteomyelitis, endocarditis, meningitis, abscesses, cystic fibrosis, gastrointestinal infections, genitourinary infections, septicemia, pharyngitis, necrotizing fasciitis, acute glomerulonephritis, otitis media, wounds, anthrax, encephalitis, diphtheria, gas gangrene, botulism and tetanus.

6. The method of claim 1 wherein the disease or infection is selected from the group consisting of gonorrhea, meningitis, pneumonia, otitis media, osteomyelitis, cystic fibrosis, genitourinary infections, peritonitis, conjunctivitis, septicaemia, venereal disease, bacteremia, nosocomial infections, dysentery, gastrointestinal infections, typhoid fever, pneumonic plague, wounds, cholera, kidney infections, meliodiosis, conjunctivitis, pertussis, tularemia, brucellosis, Legionnaire's disease, peptic ulcer disease, typhus, and pharyngitis.

7. The method of claim 1 wherein the disease or infection is contributed to or caused by an opportunistic bacterial infection.

8. The method of claim 7 wherein the disease or condition is selected from the group consisting of urinary tract infections, respiratory tract infections, dermatitis, soft tissue infections, bacteremia, bone and joint infections, gastrointestinal infections and systemic bacterial infections in patients with severe burns, cancer, cystic fibrosis or AIDS.

9. The method of claim 1 wherein the peptide, or pharmaceutically acceptable salt thereof, is administered parenterally.

10. The method of claim 1 wherein the peptide or pharmaceutically acceptable salt thereof, is administered by inhalation.

11. An aerosol formulation comprising a peptide, or a pharmaceutically acceptable salt thereof, wherein the peptide comprises 11-14 contiguous arginine residues.

\* \* \* \* \*